(12) United States Patent
Chen et al.

(10) Patent No.: US 6,780,379 B1
(45) Date of Patent: Aug. 24, 2004

(54) VOLATILE CHEMICAL REAGENT DETECTOR

(75) Inventors: Liaohai Chen, Los Alamos, NM (US); Duncan McBranch, Sante Fe, NM (US); Rong Wang, Los Alamos, NM (US); David Whitten, Sante Fe, NM (US)

(73) Assignee: The Regents of the University of California, Oakland, CA (US)

( * ) Notice: Subject to any disclaimer, the term of this patent is extended or adjusted under 35 U.S.C. 154(b) by 172 days.

(21) Appl. No.: 10/003,743

(22) Filed: Nov. 2, 2001

(51) Int. Cl.[7] .............................................. G01N 21/64
(52) U.S. Cl. ........................ 422/82.08; 844/88; 844/91
(58) Field of Search .......................... 422/82.07, 82.08, 422/82.11, 88, 91; 436/172, 106, 110, 111; 250/458.1, 459.1

(56) References Cited

U.S. PATENT DOCUMENTS

| | | | | |
|---|---|---|---|---|
| 4,892,383 A | * | 1/1990 | Klainer et al. | 385/12 |
| 5,157,261 A | * | 10/1992 | Grey et al. | 250/458.1 |
| 5,306,642 A | * | 4/1994 | Reagen et al. | 436/106 |
| 5,965,281 A | | 10/1999 | Cao | 428/690 |
| 6,024,923 A | | 2/2000 | Melendez et al. | 422/82.08 |

OTHER PUBLICATIONS

Chen, L. et al "Tuning the Properties of Conjugated Polyelectrolytes through Surfactant Complexation" J. Am. Chem. Soc., vol. 122, No. 38, pp 9302–9303 (web release date: Sep. 7, 2000).*

Chen, L. et al "Highly sensitive biological and chemical sensors based on reversible fluorescence quenching in a conjugated polymer" PNAS vol. 96, No. 22, pp. 12287–12292 (Oct. 26, 1999).*

Yang, J.S. et al "Fluorescent Porous Polymer Films as TNT Chemosensors: Electronic and Structural Effects" J. Am. Chem. Soc., vol. 120, pp 11864–11873, 1998.*

Chen, Liaohai, et al., "Surfactant–induced modification of quenching of conjugated polymer fluorescence by electron acceptors: applications for chemical sensing." Chemical Physical Letters 330 (2000) 27–33.

* cited by examiner

*Primary Examiner*—Jeffrey R. Snay
(74) *Attorney, Agent, or Firm*—Madson & Metcalf

(57) ABSTRACT

A device for detecting volatile chemical reagents based on fluorescence quenching analysis that is capable of detecting neutral electron acceptor molecules. The device includes a fluorescent material, a contact region, a light source, and an optical detector. The fluorescent material includes at least one polymer-surfactant complex. The polymer-surfactant complex is formed by combining a fluorescent ionic conjugated polymer with an oppositely charged surfactant. The polymer-surfactant complex may be formed in a polar solvent and included in the fluorescent material as a solution. Alternatively, the complex may be included in the fluorescent material as a thin film. The use of a polymer-surfactant complex in the fluorescent material allows the device to detect both neutral and ionic acceptor molecules. The use of a polymer-surfactant complex film allows the device and the fluorescent material to be reusable after exposing the fluorescent material to a vacuum for limited time.

19 Claims, 5 Drawing Sheets

VOLATILE CHEMICAL REAGENT DETECTOR

GOVERNMENT RIGHTS

This invention was made with Government support under Contract Number W-7405-ENG-36 awarded by the United States Department of Energy to The Regents of the University of California. The Government has certain rights in the invention.

BACKGROUND

1. The Field of the Invention

The present invention is related to chemical detection. More specifically, the present invention relates to devices for detecting volatile chemical reagents.

2. The Background Art

Fluorescence quenching analysis may be used to detect volatile chemical reagents. The volatile chemical reagents detected through fluorescence quenching analysis are known as electron acceptor molecules. Throughout this application, the terms volatile chemical reagent and electron acceptor molecule will be used interchangeably. Fluorescence quenching is the decrease in the fluorescent emissions intensity that occurs when an electron acceptor molecule associates with the fluorescent sites on a fluorescent material. The Stern-Volmer constant, or quenching constant, is a representation of an electron acceptor molecule's ability to quench the fluorescence of another material. The Stern-Volmer constant is often referred to as the quenching constant of a particular acceptor molecule with a fluorescent material because the constant depends on both the acceptor molecule and the fluorescent material. The quenching constant for a particular acceptor molecule can be changed by changing the fluorescent material. A fluorescent material is suitable for detecting a particular acceptor molecule only if the quenching constant of the acceptor with the material is sufficiently high to cause a detectable decrease in the fluorescent emissions intensity.

The discovery of a large quenching constant ($1.7 \times 10^7$ $M^{-1}$) between the fluorescent material poly (2,5-methoxy-propyloxysulfonate phenylene vinylene)(MPS-PPV) and the acceptor molecule methyl viologen ($MV^{2+}$) provided the basis for a new class of highly sensitive chemical detectors. This class of detectors utilized many combinations of well-known, ionic acceptors and fluorescent materials. The fluorescent materials in this class of detectors consist essentially of neat conjugated polymers.

These detectors typically comprise a neat fluorescent conjugated polymer, a means for exciting the polymer, and a means for monitoring the fluorescent emissions intensity over time as the polymer is exposed to gaseous samples. Through research and calibration prior to inclusion in a detection device, these neat conjugated polymers may be used for determining the presence and concentration of one or more volatile chemical reagents in a gaseous sample.

Neat fluorescent conjugated polymers are known to be useful in detecting methyl viologen and other ionic electron acceptors with quenching constants as high as $10^7$–$10^9$ $M^{-1}$. However, when a neutral acceptor molecule is used to quench the neat fluorescent polymer, the quenching constant can be as much as five orders of magnitude lower. For example, when MPS-PPV is quenched by a neutral acceptor molecule such as 2,4,6-trinitrotoluene (TNT) the quenching constant is $1.02 \times 10^4$ $M^{-1}$. Such a low quenching constant associated with neat fluorescent conjugated polymers renders them unsuitable for detecting neutral acceptor molecules.

A conjugated polymer's fluorescent emissions are quenched when acceptor molecules associate with the fluorescent sites on the polymer. Unfortunately, the association of the acceptor molecule with the neat polymer is mostly irreversible, even under vacuum. In some applications only 10% of the initial fluorescence can be recovered after the exposed conjugated polymer is under vacuum ($10^{-3}$ torr) for ten minutes. The difficulty in removing the acceptor molecules from the polymer may be due to changes in the morphology of the polymer or due to the strong dipole-dipole interactions between the electron rich polymer and the electron deficient acceptor molecules. Non-reversible quenching makes chemical detection through fluorescence quenching of neat conjugated polymers costly and inefficient.

A disadvantage of chemical detectors that rely on fluorescence quenching methods using neat conjugated polymers is that they are only useful for detecting charged electron acceptors. Thus, hazardous neutral chemicals such as TNT, which is a signature agent for land mine detection, are not detectable. A further disadvantage of such chemical detectors is that they are expensive and difficult to maintain. A new sample of the neat fluorescent polymer must be prepared for each subsequent use of the detection device because the fluorescent polymer used in the detection is not reusable. Furthermore, ensuring the consistency of the device is difficult because each fluorescent polymer sample must be identical to ensure identical quenching behavior.

Therefore, it would be advantageous to provide a chemical detection device capable of detecting both neutral and ionic electron acceptor molecules. It would be a further advancement to provide a fluorescence quenching detection device that is reusable. Such a device is disclosed and claimed herein.

BRIEF SUMMARY OF THE INVENTION

The present invention is directed to a device for detecting volatile chemical reagents in gaseous samples. The device utilizes a fluorescent material comprising a polymer-surfactant complex to detect specific chemical reagents within the gaseous sample. The polymer-surfactant complex is formed between a fluorescent, ionic conjugated polymer and an oppositely charged surfactant. In addition to the fluorescent material, the device further comprises a contact region where the gaseous sample may associate with the fluorescent material, a light source that emits fluorescence-inducing light directed towards the fluorescent material, and a detector that detects the fluorescent emissions intensity from the fluorescent material. The use of a fluorescent material comprising polymer-surfactant complexes enhances the material's fluorescent emissions intensity, enhances the material's quenching constant in the presence of neutral electron acceptor molecules, and allows the device to be reusable.

The fluorescent polymer-surfactant complex that is used in the fluorescent material may be formed in a polar solution. The polymer and surfactant may be added to a polar solvent to create a ratio of surfactant molecules per monomer repeat unit of polymer ranging from about 1:1 to about 1:10. One presently preferred ratio is about 1:3 when the fluorescent material includes polymer-surfactant complex solution.

Fluorescent material of the present invention may also include a polymer-surfactant complex film. The film may be a bilayer film with an outer layer of oppositely charged surfactant covering a film of fluorescent, ionic conjugated polymer.

The film used in the fluorescent material may also be formed from a solid precipitate that is formed by complexing a fluorescent, ionic conjugated polymer with a sufficient quantity of oppositely charged surfactant to cause precipitation. The precipitate may be formed by complexing the polymer and surfactant in a ratio of surfactant molecules per monomer repeat unit of polymer of about 1:1. The film formed from the precipitate may be formed by spin coating the precipitate from a solvent, by casting, or by other methods known in the art.

The light source directed at the fluorescent material emits at least a portion of its light at the excitation wavelength of the polymer-surfactant complex causing it to fluoresce.

The detector may comprise a detection device and an output device. The detection device receives fluorescent emissions from the polymer-surfactant complex, converts the emission intensity into electronic signals, and communicates the electronic signals to the output device. The output device transmits the intensity of the fluorescent emissions received by the detection device for analysis.

The present invention is also directed towards a reusable device for detecting volatile chemical reagents in a gaseous sample. A vacuum evacuates the gaseous sample from the region of the fluorescent material after the material has been exposed to the gaseous sample.

BRIEF DESCRIPTION OF THE DRAWINGS

A more particular description of the invention briefly described above will be rendered by reference to the appended drawings. Understanding that these drawings only provide information concerning typical embodiments of the invention and are not therefore to be considered limiting of its scope, the invention will be described and explained with additional specificity and detail through the use of the accompanying drawings, in which.

It should be understood that the drawings of the devices are not necessarily to scale and that the embodiments are sometimes illustrated by graphic symbols, diagrammatic representations; and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE PREFERRED EMBODIMENTS

A preferred embodiment of the invention is now described with reference to the FIGS. 1–5, where like reference numbers indicate identical or functionally similar elements. The components of the present invention, as generally described and illustrated in the Figures, may be implemented in a wide variety of configurations. Thus, the following more detailed description of the embodiments of the system and method of the present invention, as represented in the Figures, is not intended to limit the scope of the invention, as claimed, but is merely representative of presently preferred embodiments of the invention.

Figure 1:
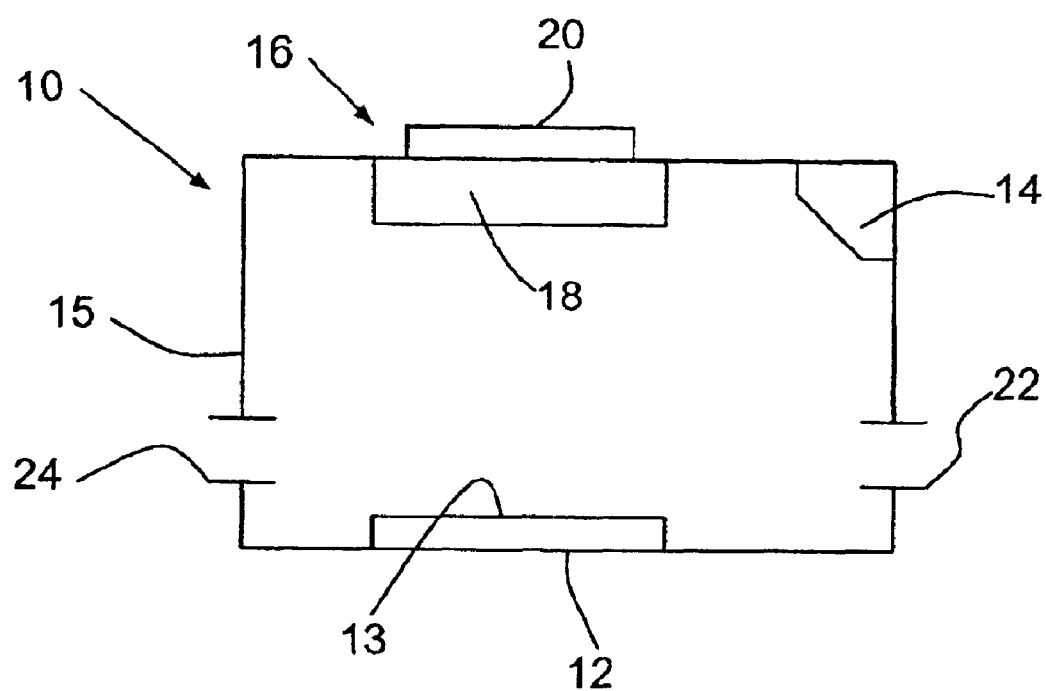
FIG. 1 is a schematic representation of an embodiment within the scope of the present invention.

Referring to FIG. 1, an embodiment of a device for detecting volatile chemical reagents is shown. The device 10 comprises a fluorescent material 12, a contact region 13 where a gaseous sample may associate with the fluorescent material 12, a light source 14 that emits light to excite the fluorescent material 12 and cause it to fluoresce, and a detector 16 that detects fluorescent emissions from the fluorescent material 12.

The fluorescent material 12 comprises at least one polymer-surfactant complex formed by combining a fluorescent, ionic conjugated polymer and an oppositely charged surfactant. The use of polymer-surfactant complexes rather than neat polymers in the fluorescent material 12 that allows devices 10 within the scope of the present invention to detect both neutral and ionic electron acceptor molecules.

The quenching constants between neutral electron acceptor molecules and neat polymers are too low for neat polymers to reliably detect neutral acceptors. However, the quenching constant increases rapidly as an oppositely charged surfactant is added to a fluorescent, ionic conjugated polymer. The addition of an oppositely charged surfactant to a fluorescent, ionic conjugated polymer to create the polymer-surfactant complex may improve the neat polymer's quenching constant for neutral acceptor molecules by over. 800%. Neutral acceptor molecules whose quenching constants are notably improved include, but are not limited to, nitroaromatics and cyanoaromatics. This improvement in the quenching constant for neutral acceptors allows the devices within the scope of the present invention to effectively detect neutral acceptors that were previously undetectable through fluorescence quenching analysis.

The polymer-surfactant complexes included in the fluorescent material 12 may be formed in a polar solution. Water is a presently preferred solvent. Other polar solvents may also be used, including, but not limited to tetrahydrofuran (THF), dioxane, N, N-dimethylformamide (DMF), N, N,-dimethylacetamide (DMAC), N-methylpyrrolidone (NMP), dimethylsulfoxide (DMSO), acetone, or a lower alkyl alcohol ($C_1$ to $C_4$). Mixtures of solvents may be used. Without being bound by theory, it is currently believed that a solution with a ratio of surfactant molecules per monomer repeat unit of polymer ranging from about 1:1 to about 1:10 is preferred. A ratio of 1:3 may be preferred when the fluorescent material 12 includes a polymer-surfactant complex solution.

The polymer used to form the polymer-surfactant complex may be any ionic conjugated polymer or polyelectrolyte having fluorescent properties. Many ionic conjugated polymers have fluorescent properties, including, but not limited to, substituted and unsubstituted forms of poly(phenylene vinylene), poly(silyl-phenylene vinylene), poly(thienylene vinylene), poly(naphthalene vinylene), poly(quinoline vinylene), poly(pyridine vinylene), poly(fluorene), poly (thiophene), and derivatives thereof. The polymer will typically have an ionic side chain or ionic moieties that interact with the oppositely charged surfactant.

The surfactant used in the present invention has a charge opposite that of the polymer. Surfactants with an alkyl chain length ranging from about 8 to about 16 carbons are particularly effective. Surfactants with an alkyl chain length of less than about 8 carbons produce smaller effects on the fluorescent emissions intensity and quenching sensitivity than do surfactants that have between 8 and 16 carbons. Also, surfactants with chain lengths longer than about 18 carbons produce smaller effects than do surfactants with an alkyl chain length between 8 and 16 carbons.

The fluorescent material 12 may also include films of polymer-surfactant complex formed in a variety of ways to produce fluorescent materials 12 that may be reusable. The polymer-surfactant complex film may be created from the polymer-surfactant complex precipitate formed as the ratio of surfactant molecules per monomer repeat unit of polymer approaches about 1:1. Once the precipitate is recovered, it may be formed into thin films through a variety of methods known in the art, such as casting or coating from an organic solvent.

Polymer-surfactant complex films may also be created by coating a substrate with a fluorescent ionic conjugated polymer via electrostatic self-assembly, spin casting, coating, or other methods known in the art. The layer of ionic, conjugated polymer is then covered with a layer of oppositely charged surfactant. The surfactant may be layered on top of the polymer film by dipping the polymer-coated substrate into a solution of oppositely charged surfactant. This creates a bilayer film of polymer-surfactant complex on a substrate with the surfactant forming the exterior layer.

The ability to fabricate the fluorescent materials 12 in a variety of ways allows them to be used in diverse sensing applications and in a wide range of sensing devices. Various important fluorescent properties are enhanced when the fluorescent materials 12 include the polymer-surfactant complexes disclosed herein.

Figure 2:
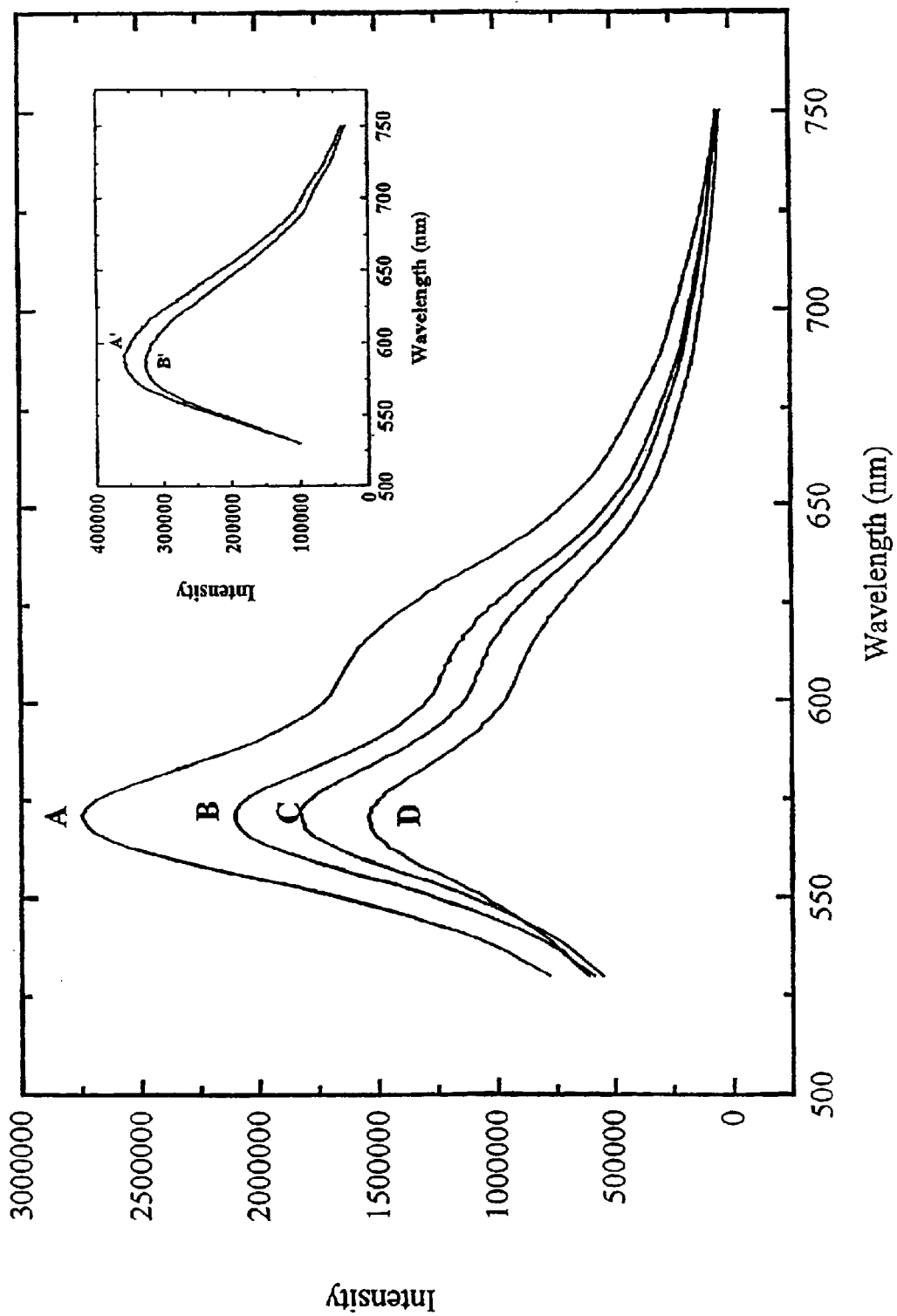
FIG. 2 is a graph showing the change of the emission spectra of MPS-PPV and DTA complex in water ([MPS-PPV]=$1.5 \times 10^{-5}$ M; [DTA]=$5 \times 10^{-6}$ M) at different concentrations of TNT; the inset shows the emission spectra of MPS-PPV ([MPS-PPV]=$1.5 \times 10^{-5}$ M) in water.

FIG. 2 shows the differences in fluorescence intensity and quenching sensitivity between the neat polymer poly(2,5-methoxy-propyloxysulfonate phenylene vinylene (MPS-PPV) and the polymer-surfactant complex formed between the polymer MPS-PPV and the surfactant dodecyltrimethylammonium bromide (DTA). The polymer-surfactant complex MPS-PPV/DTA is an example of the complexes that may be formed according to the above procedures and used in devices 10 within the scope of the present invention and is not to be considered as a limitation.

The main window in FIG. 2 shows the fluorescent emissions spectra for the MPS-PPV/DTA complex in the presence of varied concentrations of the neutral electron acceptor 2,4,6-trinitrotoluene (TNT). The inset window of FIG. 2 shows the fluorescent emissions spectra for the corresponding neat polymer MPS-PPV. In the main window, curve A shows the complex's emission spectra in the presence of no TNT (0 M); curve B shows the emission spectra in a TNT concentration of $1.3 \times 10^{-7}$ M; curve C shows the emission spectra in a TNT concentration of $3.8 \times 10^{-7}$ M; and curve D shows the emission spectra in a TNT concentration of $8.5 \times 10^{-6}$ M. In the inset window, curve A' shows the neat polymer's emission spectra in the presence of no TNT (0 M) and curve B' shows the emission spectra in a TNT concentration of $8.5 \times 10^{-6}$ M. With reference to these two graphs and the corresponding intensity scales shown on the y-axis, it is observed that the fluorescence intensity of the polymer-surfactant complex is nearly ten times greater than the intensity of the neat polymer. It is also important to note that curve D of the polymer-surfactant complex and curve B' of the neat polymer show the emission spectra in the same concentration of TNT.

FIG. 2 shows that the polymer-surfactant complexes are better suited to detect neutral chemical reagents because the change in fluorescent emission intensity, known as fluorescence quenching, from A to D ($\sim 1.2 \times 10^6$) is much greater than the change between A' and B' ($\sim 3 \times 10^4$).

The increase in quenching sensitivity to neutral electron acceptor molecules allows devices using polymer-surfactant complexes in the fluorescent material 12 to efficiently detect neutral electron acceptor molecules. Devices 10 within the scope of the present invention incorporating polymer-surfactant complexes in the fluorescent material 12 are able to detect both neutral and ionic acceptor molecules in gaseous samples because the quenching constants for both types of acceptor molecules are on the same scale.

Figure 3B:
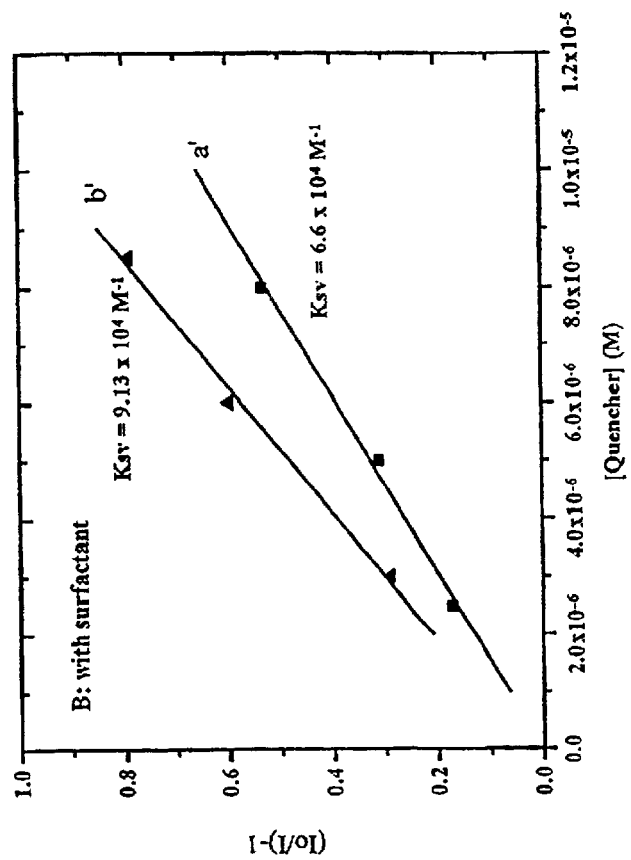
FIG. 3B is a Stern-Volmer quenching curve for the polymer-surfactant complex MPS-PPV/DTA with a') $MV^{2+}$, b') TNT.
Figure 3A:
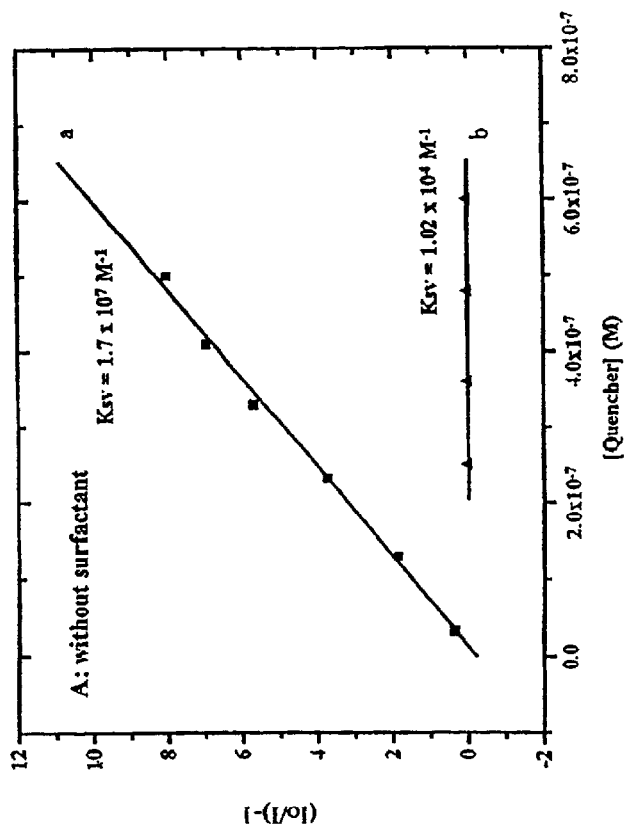
FIG. 3A is a Stern-Volmer quenching curve for the neat polymer MPS-PPV with a) $MV^{2+}$, b) TNT.
Figure 4:
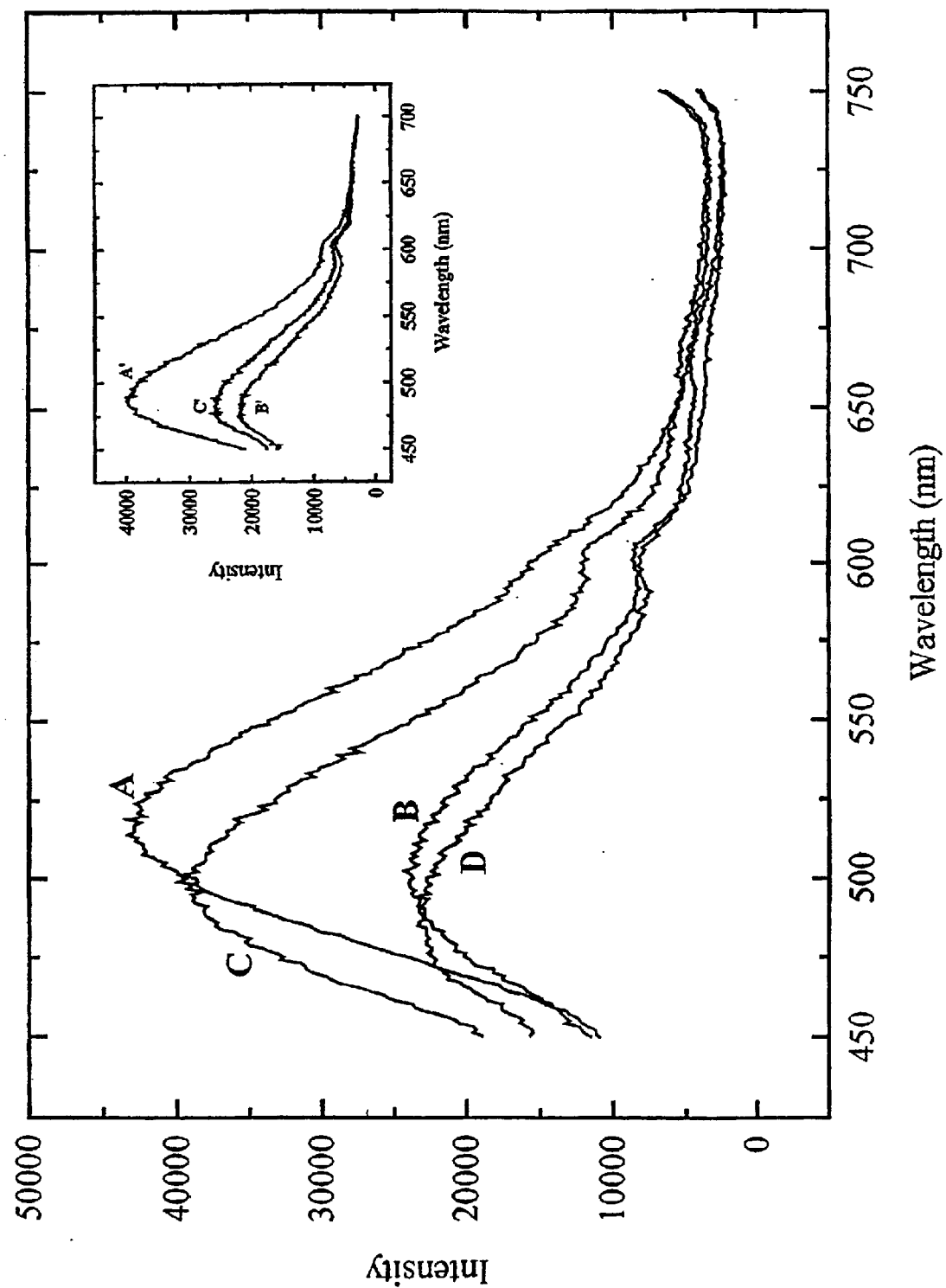
FIG. 4 is a graph showing the emission of spectra of the polymer-surfactant complex bilayer film MPS-PPV/DTA; the inset shows the emission spectra of a film of the neat polymer MPS-PPV.

FIGS. 3A and 3B illustrate that addition of an oppositely charged surfactant to an ionic conjugated polymer changes the quenching constants for both ionic and neutral electron acceptor molecules. FIG. 3A shows the quenching curves for a neat polymer (MPS-PPV) with (a) an ionic acceptor molecule ($MV^{2+}$) and (b) a neutral acceptor molecule (TNT). The significant difference in the slopes of the two curves is indicative of the large difference in quenching constants; the ratio of quenching constants in this figure is approximately $1.5 \times 10^3$ $M^{-1}$. FIG. 3B, however, shows that the quenching curves are significantly changed for a polymer-surfactant complex (MPS-PPV/DTA) in the presence of the same electron acceptor molecules. There is very little difference in the slopes of the two curves in FIG. 3B; the ratio of quenching constants in this figure is approximately 0.73. The devices within the scope of the present invention may effectively detect both neutral and ionic electron acceptor molecules because the quenching constants for both acceptor molecules are on the same scale.

Using fluorescence quenching analysis to detect chemical reagents is based on the ability to detect the decrease in fluorescence intensity, or quenching, upon exposure of the fluorescent material to the acceptor molecules. The fluorescence intensity of the polymer-surfactant complexes used in the present invention is detectably quenched upon exposure to a gaseous sample that contains volatile chemical reagents. However, the fluorescence of the polymer-surfactant complex must be recovered before the complex can be reused for chemical detection. Recovering the fluorescence intensity has been a problem in all detectors that are based on fluorescence quenching.

The problem of recovering the fluorescence intensity may be obviated by complexing an ionic conjugated polymer with an oppositely charged surfactant. The surfactant's interaction with the polymer in the polymer-surfactant complex acts as a barrier between the electron acceptor molecules and the polymer's fluorescence sites. Without being bound by theory, it is currently believed that the surfactant positions itself between the acceptor molecule and the polymer such that the fluorescence is quenched without the acceptor becoming fixedly attached to the polymer. Thus, the fluorescence of the polymer-surfactant complexes used in the devices 10 of the present invention is recoverable to a much greater degree than if the devices utilized neat polymers. When a polymer-surfactant complex is incorporated into the fluorescent materials 12 as a film, the recovery is generally greater than 80% and may approach 100% recovery. Devices with a fluorescence recovery greater than 80% may be called reusable devices.

FIG. 4 shows a graph of the fluorescent emission intensity for a polymer-surfactant complex film prepared according to the bi-layer film procedures described above, while the inset to FIG. 4 shows the fluorescent emission intensity for a similar film formed from a neat polymer without the surfactant layer. In the main window of FIG. 4, curve A shows the fluorescence intensity before exposure to 2,6-dinitrotoluene (DNT) vapor; curve B shows the intensity upon exposure for 10 seconds to DNT vapor; curve C shows the intensity after vacuum treatment at $10^{-3}$ torr for 10 minutes; and curve D shows the intensity after another exposure for 10 seconds to DNT vapor. In the emission intensity spectra for a neat polymer shown in the inset window of FIG. 4, curve A' shows the fluorescence intensity before exposure to DNT vapor; curve B' shows the intensity after exposure for 10 seconds to DNT vapor; and curve C' shows the intensity after vacuum treatment at $10^{-3}$ torr for 10 minutes. From FIG. 4 it is clear that the use of polymer-surfactant complexes in devices within the scope of this invention significantly increases the reusability of the devices.

Figure 5:
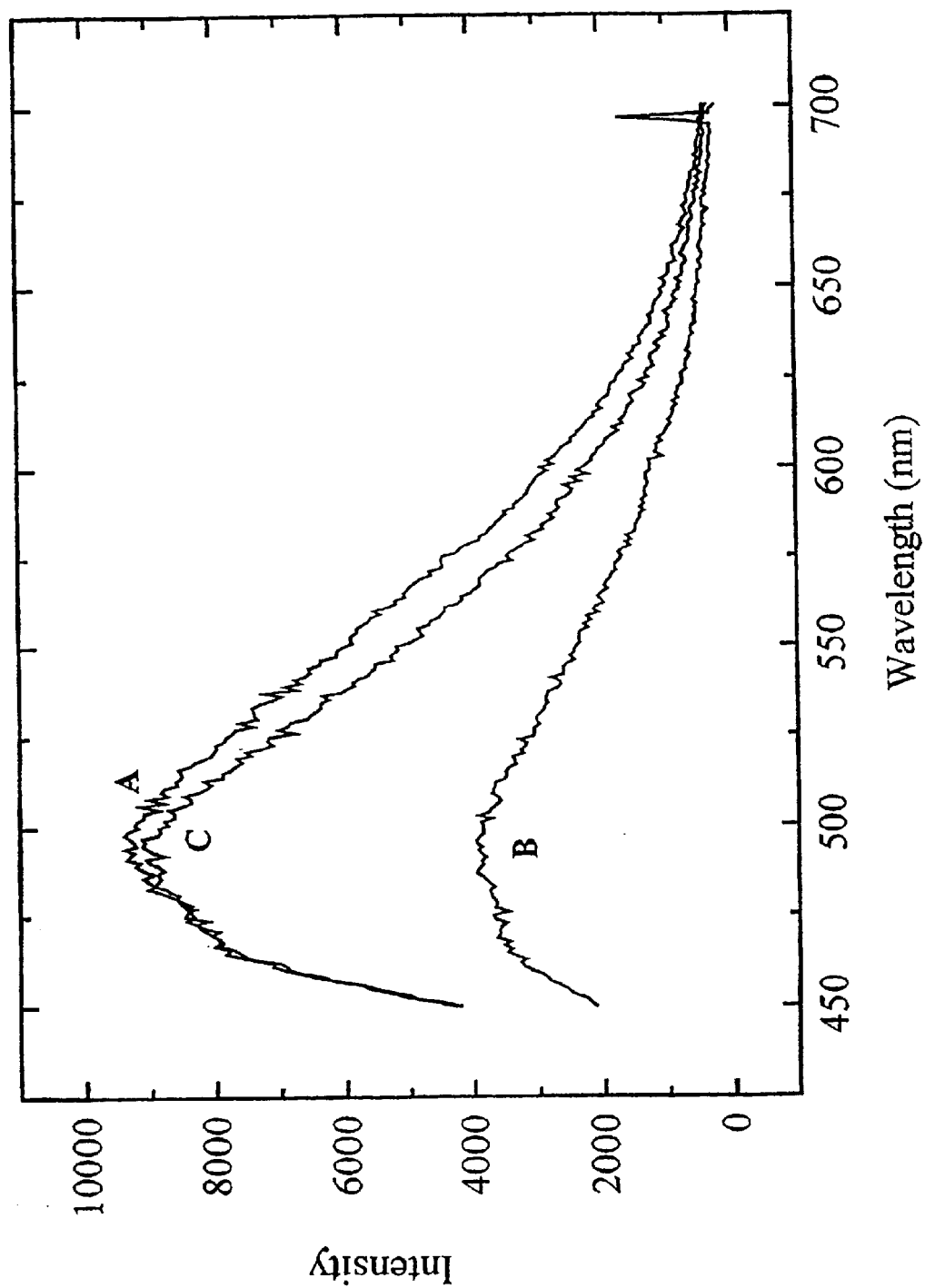
FIG. 5 is a graph showing the emission spectra of a cast film formed from the precipitate of MPS-PPV/DTA.

FIG. 5 shows the emission intensity spectra for films formed from the polymer-surfactant complex precipitate. In FIG. 5, curve A shows the fluorescence intensity before exposure to DNT vapor; curve B shows the intensity after exposure for 10 seconds to DNT vapor; and curve C shows the intensity after vacuum treatment at $10^{-3}$ torr for 10 minutes. FIG. 5 shows that such films are reusable because the fluorescence intensity is up to 98% recoverable. Chemical detection devices 10 within the scope of the present invention can be made reusable by incorporating fluorescent materials 12 that include polymer-surfactant complex films formed as a single film from the precipitate, as a bi-layer film, or through other methods known in the art.

FIG. 1 illustrates a chemical detection device 10 incorporating fluorescent material 12 within supporting structures 15. Also shown in FIG. 1 is a contact region 13 where a gaseous sample may associate with the fluorescent material 12, a light source 14 that emits light to excite the fluorescent material 12 and cause it to fluoresce, and a detector 16 that detects fluorescent emissions from the fluorescent material 12. The chemical detection device 10 in FIG. 1 also includes an inlet 22 and an outlet 24. One of ordinary skill in the art will recognize that the supporting structures 15 and other elements 12, 13, 14, 16 can be arranged in a variety of shapes and arrangements for different chemical detection applications.

The fluorescent material 12 shown in FIG. 1 may be incorporated in the device 10 in a variety of shapes and locations. The fluorescent material 12 of the present invention comprises at least one polymer-surfactant complex, often as a film or solution. The fluorescent material 12 has a contact region 13 where the polymer-surfactant complex can associate with the volatile chemical reagent or gaseous sample to be analyzed.

If the polymer-surfactant complex is in solution, the solution may be in a suitable container that permits exposure to gaseous sample which may quench fluorescence of the polymer-surfactant complex. The polymer-surfactant complex in the fluorescent material 12 may preferably be a film formed in one of the ways previously discussed. Another advantage to the use of polymer-surfactant complex films is the film's adaptability to various configurations and embodiments allowing these fluorescent materials 12 to be incorporated into many types of chemical detection devices.

Alternatively, the fluorescent material 12 may be formed of an array of polymer-surfactant complex films. As used herein, an array of films means that at least two polymer-surfactant complex films operate together to form the fluorescent material 12. The use of an array may be desirable for the possibility of incorporating a variety of films, each film containing different polymer-surfactant complexes. The use of an array comprising a variety of polymer-surfactant complexes will allow a single detection device 10 to detect the presence of multiple volatile chemical reagents, both ionic and neutral electron acceptor molecules.

FIG. 1 also shows a light source 14 that emits light in the direction of the fluorescent material 12. A substantial quantity of the light emitted from the light source 14 is preferably at the excitation wavelength of the fluorescent polymer-surfactant complex, though all that is necessary is that a sufficient amount of the light be at the excitation wavelength such that the polymer-surfactant complex is excited and caused to fluoresce. The light source 14 may include suitable optical lenses to focus the light onto the contact region 13. It is important to note that the exact position of the light source 14 in FIG. 1 relative to the remaining elements is by way of example and not to be considered limiting. The light source 14 may be located in a variety of locations and orientations provided that its emitted light, either directly or indirectly, causes the polymer-surfactant complex to fluoresce. It is to be observed that there are many suitable light sources known in the art that may be configured in a variety of ways to serve as the light source 14.

FIG. 1 further shows a detector 16 positioned to receive fluorescent emissions from the fluorescent material 12. The detector 16 may be configured to monitor and measure the intensity of the fluorescent emissions. The detector 16 may additionally be configured to convey the measured intensities to an observer or to a recording device for analysis. The detector 16 may comprise a detection device 18 and an output device 20. The detector 16 is preferably configured such that the detection device 18 can receive fluorescent emissions, determine their intensity, and convey emission intensity data to the output device 20. The output device 20 may convey information to an observer, to a recording system, or to a remote location. The detection devices 18 to be used in the present invention are well known in the art, such as digital and analog optical sensors, as are the output devices 20.

With continued reference to FIG. 1, when the supporting structures 15 of the device 10 form an enclosure it is important that the device 10 also comprise an inlet 22 through which the gaseous sample may enter the enclosure and an outlet 24. The inlet 22 and the outlet 24 may be positioned such that the gaseous sample flowing through the device 10 pass by the contact region 13 to associate with the fluorescent material 12. The inlet and outlet 22, 24 may be simple openings in the enclosure 15 such that open air transport of the gaseous sample into the enclosure is possible. This arrangement of the ports 22, 24 may be preferred if the device is to be placed in a remote area that is suspected to be unsafe for manual operation of the detection device 10. An embodiment with open air transport through the inlet 22 and outlet 24 combined with an output device 20 capable of transmitting fluorescent emission intensity data to distant locations may enable a user to detect the presence of harmful volatile chemical reagents remotely. The inlet and outlet 22, 24 may be coupled via tubing to a gaseous sample. Valves and pumps (not shown) may be utilized to move the gaseous sample through the device 10. It is to be observed that, regardless of the configuration of the various elements, the fluorescent material 12 must be accessible by the gaseous sample.

The chemical detection device 10 is preferably reusable. In such an embodiment, the device is preferably enclosed, with the inlet 22 and outlet 24 being coupled to suitable tubing, injectors, or collection devices. The gaseous sample may be withdrawn from the device 10 after the sample has had an opportunity to associate with the fluorescent material 12 at the contact region 13. The outlet 24 is preferably coupled to a vacuum or other device known in the art adapted to withdraw gases from the device 10. The vacuum device is used to evacuate the gaseous sample from the region around the fluorescent material 12. The inlet and outlet 22, 24 may be operated manually or may be configured to be remotely operated by a user in a safe location for analysis of potentially harmful gases.

A reusable detection device 10 preferably contains reusable fluorescent materials 12. As discussed above, more than 80% of the fluorescence of polymer-surfactant complex films used in the fluorescent material 12 may be recovered when the material 12 is exposed to a vacuum. The quenched fluorescence intensity can be recovered by removing the quenching chemical reagent from the region around the fluorescent material 12. The vacuum device associated with the outlet port 24 is preferably configured to evacuate the gaseous sample from the space within the device 10. The strength and duration of the vacuum applied by the vacuum device may vary depending on the type of polymer-surfactant complex used and chemical reagent that is to be detected. Without being bound by theory, it is currently believed that a vacuum of about $10^{-3}$ torr for about 10 minutes will recover a sufficient percentage of the quenched fluorescent emissions intensity such that the fluorescent material 12 and the device 10 may be reusable.

The supporting structures 15 of the device 10 are drawn in a simple shape to more clearly illustrate the coordinating elements. However, chemical detection devices within the scope of the present invention may incorporate supporting structures 15 to form spherical, cubical, polygonal, or other shapes. One of ordinary skill in the art will recognize that chemical detection devices incorporating fluorescent materials 12 comprising at least one polymer-surfactant complex are within the scope of the present invention. One of ordinary skill will also recognize that the chemical detection device 10 of the present invention can be miniaturized and included in a more portable device or even in a handheld apparatus.

It should be appreciated that the apparatus and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive and the scope of the invention.

What is claimed is:

1. A device for detecting volatile chemical reagents in a gaseous sample, comprising:
    a fluorescent material comprising at least one polymer-surfactant complex disposed as a thin film comprising:
        a fluorescent, ionic conjugated polymer; and
        an oppositely charged surfactant;
    a contact region where a gaseous sample may associate with the polymer-surfactant complex;
    a light source that emits light to excite the polymer-surfactant complex and cause it to fluoresce; and
    a detector that detects the fluorescent emissions intensity from the polymer-surfactant complex.

2. The device of claim 1, wherein the detector comprises a detection device and an output device.

3. The device of claim 2, wherein the output device displays the fluorescent emissions intensity.

4. The device of claim 2, wherein the output device transmits the fluorescent emissions intensity to a remote location.

5. The device of claim 2, wherein the output device records the fluorescent emissions intensity for later analysis.

6. The device of claim 2, further comprising:
    at least one support structure;
    an inlet; and
    an outlet.

7. The device of claim 6, wherein the support structure encloses the detection device, light source, contact region, and the fluorescent material; and wherein the inlet and outlet allow the gaseous sample pass by the contact region and associate with the polymer-surfactant complex.

8. A device for reusably detecting volatile chemical reagents in a gaseous sample, comprising:
    a fluorescent material comprising at least one polymer-surfactant complex disposed as a thin film comprising:
        a fluorescent, ionic conjugated polymer; and
        an oppositely charged surfactant;
    a contact region where the gaseous sample may associate with the polymer-surfactant complex;
    a light source that emits light to excite the polymer-surfactant complex and cause it to fluoresce;
    a detector that detects the fluorescent emissions from the polymer-surfactant complex; and
    a vacuum device configured to evacuate the gaseous sample from the region of the polymer-surfactant complex after the complex has been exposed to the gaseous sample.

9. The device of claim 8, wherein the polymer-surfactant film is a bilayer in which a film of the fluorescent, ionic conjugated polymer is covered by an outer layer of the oppositely charged surfactant.

10. The device of claim 8, wherein the polymer-surfactant film is a solid precipitate that is formed by complexing the fluorescent, ionic conjugated polymer with a sufficient quantity of the oppositely charged surfactant.

11. The device of claim 10, wherein the polymer-surfactant film is prepared by spin coating the solid precipitate from a solvent.

12. The device of claim 10, wherein the polymer-surfactant film is cast from the solid precipitate.

13. The device of claim 10, wherein the solid precipitate is formed by complexing the polymer and surfactant in a ratio of surfactant molecules per monomer repeat unit of polymer of about 1:1.

14. The device of claim 8, wherein the detector comprises a detection device and an output device.

15. The device of claim 14, wherein the output device displays fluorescent emissions intensity received by the detection device from the polymer-surfactant complex.

16. The device of claim 14, wherein the output device records fluorescent emissions intensity received by the detection device from the polymer-surfactant complex.

17. The device of claim 14, wherein the output device transmits fluorescent emissions intensity received by the detection device from the polymer-surfactant complex to a remote location.

18. The device of claim 8, wherein the fluorescent material comprises an array of polymer-surfactant complex films.

19. The device of claim 18, wherein each polymer-surfactant complex film comprises a different polymer-surfactant complex, and wherein the array of polymer-surfactant complex films and the detector are configured such that the detector can detect the presence and concentration of various volatile chemical reagents.

* * * * *